(12) United States Patent
Wyatt et al.

(10) Patent No.: US 7,405,558 B2
(45) Date of Patent: Jul. 29, 2008

(54) STEAM GENERATOR MAPPING WITH REFLECTIONS OF EDDY CURRENT SIGNAL

(75) Inventors: Joseph R. Wyatt, Lynchburg, VA (US); John Griffith, Lynchburg, VA (US); Victor Newman, Forest, VA (US); Jeffrey M. Fleck, Forest, VA (US)

(73) Assignee: Areva NP, Inc., Lynchburg, VA (US)

( * ) Notice: Subject to any disclaimer, the term of this patent is extended or adjusted under 35 U.S.C. 154(b) by 37 days.

(21) Appl. No.: 11/484,227

(22) Filed: Jul. 10, 2006

(65) Prior Publication Data

US 2008/0007257 A1 Jan. 10, 2008

(51) Int. Cl.
*G01N 27/72* (2006.01)
(52) U.S. Cl. .................... 324/228; 324/242; 324/262
(58) Field of Classification Search ............... 324/228, 324/242, 262
See application file for complete search history.

(56) References Cited

U.S. PATENT DOCUMENTS 5,581,037 A * 12/1996 Kwun et al. ............... 73/623
6,271,670 B1 * 8/2001 Caffey ...................... 324/642

OTHER PUBLICATIONS

Framatome ANP (now AREVA NP), "Modeling of Upper Bundle Deposits", Carl Thurston, presented at the EPRI Steam Generator Secondary Side Management Conference, Feb. 10-12, 2003.

Westinghouse, "A Strategic Thinking to Draw Benefit from Tube Scale for Boiling Enhancement", M. H. Hu, presented at the EPRI Steam Generator Secondary Side Management Conference, Feb. 10-12, 2003.
Dominion Engineering, Inc., "Thermal Performance Trends in Replacement Steam Generators", Marc Kreider, Glenn White and Robert Varrin, Jr., presented at the EPRI Steam Generator Secondary Side Management Conference, Feb. 10-12, 2003.
Dominion Engineering, Inc., "Economic Evaluation of Steam Generator Secondary Management Strategies at Plant Vogtle", Marc Kreider, Glenn White and Robert Varrin, Jr., presented at the EPRI Steam Generator Secondary Side Management Conference, Feb. 10-12, 2003.
Westinghouse, "Scale Profiling Coupled with Quatrefoil Blockage Assessment Technology and Visual Inspection", Susan Wozniak, Earl Morgan, Dan Yaklich, John Balavage, Jon.Barkich and Chris Hu, presented at the 23rd Steam Generator NDE Workshop, Jul. 12-14, 2004.

* cited by examiner

*Primary Examiner*—Reena Aurora
(74) *Attorney, Agent, or Firm*—Kenyon & Kenyon LLP (57) ABSTRACT

A method to determine deposits in a steam generator having the steps of creating a calibration standard having at least two rings of deposit material, subjecting the calibration standard to an eddy current signal, wherein an amplitude of the signal reflected from the calibration standard is used to obtain a polynomial equation fit of the reflected eddy current signals to actual thickness of the rings, obtaining a steam generator with tubes, initiating an eddy current signal into the tubes of the steam generator, detecting and recording reflections of the eddy current signal initiated into the tubes of the steam generator, and determining a thickness of the deposits in the steam generator from the recorded reflections of the eddy current signal and the polynomial equation.

6 Claims, 5 Drawing Sheets

STEAM GENERATOR MAPPING WITH REFLECTIONS OF EDDY CURRENT SIGNAL

FIELD OF THE INVENTION

The present invention relates to steam generators. More specifically, the present invention provides a steam generator deposit mapping system and methodology.

BACKGROUND INFORMATION

Nuclear steam generators used in pressurized water reactors, for example, are subject to the accumulation of feedwater impurities. Although the feedwater is maintained at a high level of purity, minute concentrations of corrosion products and/or feedwater impurities may be concentrated in the flow stream, consequently leading to buildup of these materials within the steam generator as the water is converted into steam. These deposits will eventually degrade the thermal hydraulic performance of the component.

To increase the heat transfer capabilities of the steam generator, the thickness of the deposits, as well as the locations of the deposits, must be determined such that removal techniques may be implemented. Currently, visual inspections and eddy current inspections are utilized to ascertain locations and approximate thickness of material. These techniques, however, are prone to error. Moreover, visual inspections introduce a significant radiological risk to workers if the steam generator is connected to a nuclear power generation system.

There is therefore a need to provide a system that will determine the thickness of deposit accumulations as well as the location of those accumulations on the heating surfaces of a steam generator.

There is also a need to provide a system that will determine the accumulations of deposits on the heating surfaces of the steam generator, while minimizing the need for worker ingress into a potentially radioactive environments.

SUMMARY

It is therefore an objective of the present invention to provide a system that will determine the thicknesses of these accumulations of deposits as well as the location of those accumulations on the heating surfaces of a steam generator.

It is also an objective of the present invention to provide a system and methodology that will calculate accumulations of deposits on the heating surfaces of the steam generator, while minimizing the need for ingress into a potentially radioactive environment for workers.

The objectives described above are achieved as illustrated and described. The methodology according to the present invention determines the thickness and location of deposits in a steam generator. The methodology comprises the steps of creating a calibration standard having at least two rings of deposit material, subjecting the calibration standard to an eddy current signal, wherein an amplitude of the signal reflected from the calibration standard is used to obtain a polynomial equation fit of the reflected eddy current signals to actual thickness of the rings, obtaining a steam generator with tubes, initiating an eddy current signal into the tubes of the steam generator, detecting and recording reflections of the eddy current signal initiated into the tubes of the steam generator, and determining a thickness of the deposits in the steam generator from the recorded reflections of the eddy current signal and the fourth order polynomial equation.

The methodology may be performed such that the eddy current signal is created by a bobbin coil probe.

The method may also be accomplished such that the polynomial equation is a fourth order equation.

The method also may be accomplished such that multiple signals are input into the calibration standard and reflected signals are detected and processed to obtain the polynomial equation. Additionally, multiple reflected signals may be passed through a culling algorithm.

A second alterative method may also be performed. The method comprises creating a calibration standard having at least two rings of deposit material, subjecting the calibration standard to an eddy current signal, wherein an amplitude of the signal reflected from the calibration standard is used to obtain a polynomial equation fit of the reflected eddy current signals to actual thickness of the rings, obtaining a baseline signal offset from the calibration standard; obtaining a steam generator with tubes, initiating an eddy current signal into the tubes of the steam generator, detecting and recording reflections of the eddy current signal initiated into the tubes of the steam generator; subtracting the baseline signal offset from the reflected eddy current signals to obtain a corrected reflected eddy current signal, and determining a thickness of the deposits in the steam generator from the corrected reflected eddy current signal through the polynomial equation.

DETAILED DESCRIPTION

Figure 5:
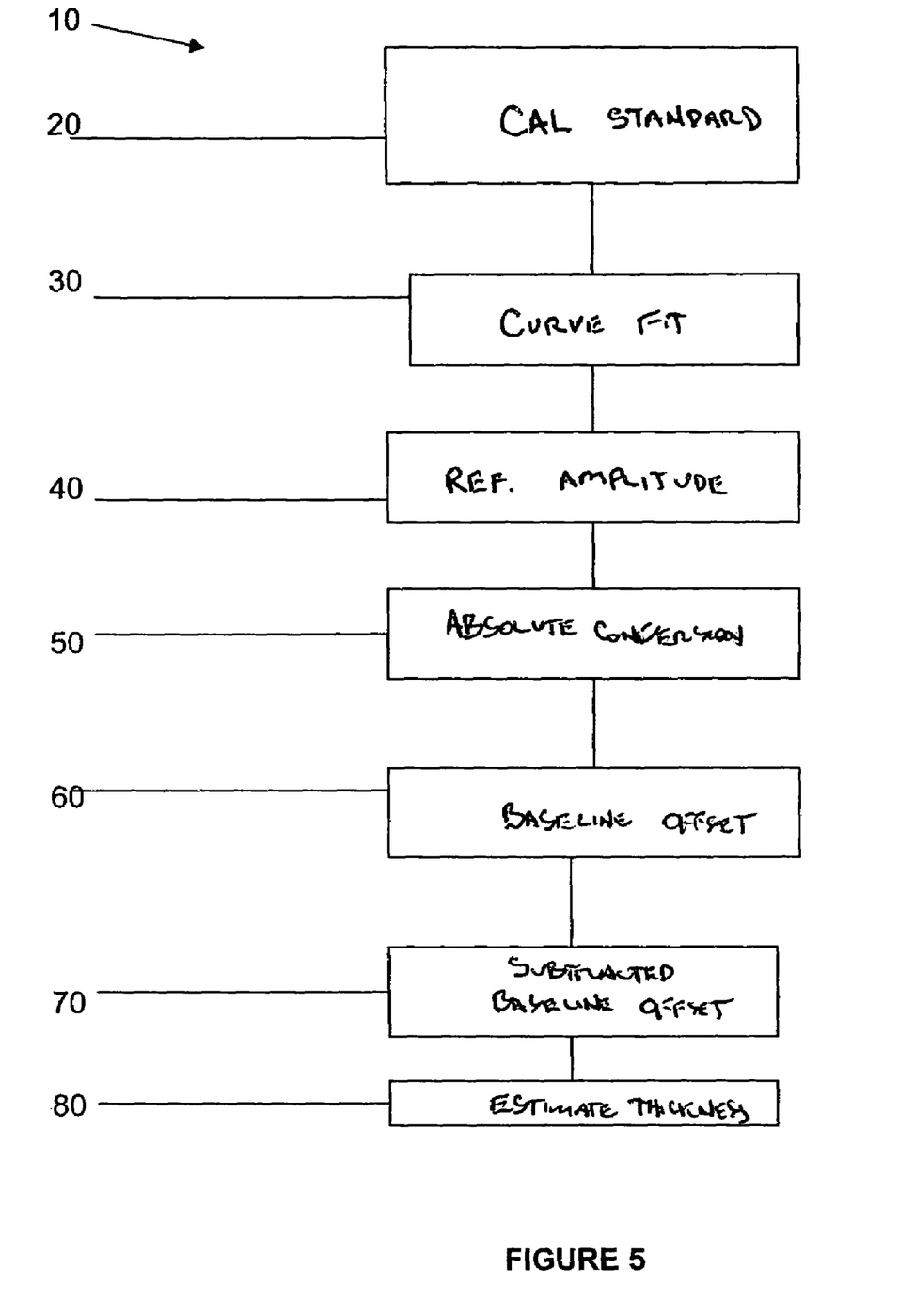
FIG. 5 is a diagram of the method to determine deposit mapping inside a steam generator.

Referring to FIG. 5, a deposit mapping methodology 10 is provided to ascertain the location and amounts of accumulated material inside a steam generator. The steam generator may be part of a nuclear or non-nuclear system. The accumulated material may be from corrosion products generated inside the plant as well as feedwater impurities inside the coolant as it flows through the steam generator.

The purpose of the deposit mapping methodology 10 is to provide characterization of the amounts of deposit loading as well as the deposit distribution of materials present in a steam generator as the feedwater passes through a steam generator. Knowledge of the deposit condition within a steam generator is valuable for assessing the impact of the deposit on thermal hydraulic performance, on the potential for accelerated corrosion of the heating surfaces within the steam generator, as well as determining a degradation of Non Destructive Examination (NDE) signal detection performance. This information is also necessary for determining the best maintenance techniques for mitigating the deposit condition and for assessing the effectiveness of such maintenance actions.

The deposit mapping process utilizes three key components. The combination of the three components yields a unique methodology for measuring the amount of deposit adhered to the outer diameter surface of steam generator tubing.

In the first methodology step, a specific deposit calibration standard 20 is created. The standard 20 is derived from a quantity of circumferential rings of deposit material, wherein each ring contains a known amount of deposit material as determined by thickness of each of the rings. The thickness measurements for the calibration standard are predetermined or pre-measured to ascertain the thickness of each ring. The series of rings in the exemplary embodiment have an increasing amount of deposit volume and thickness progressing from the inner most circle to the outermost circle. In the exemplary embodiment, the rings are separated sufficiently to allow for the signal response from a bobbin eddy current probe to achieve a non-deposit influence null value between each ring. The current deposit calibration standard design in the exemplary embodiment disclosed utilizes five deposit rings and six non-deposit influenced null regions. The deposit material mixture is determined from specific plant chemistry to assure consistent signal response between the calibration standard and the steam generator tubing.

After creation of the above calibration standard 20, the next step is evaluating the standard with a bobbin eddy current probe. A bobbin eddy current signal amplitude reflected from each deposit ring relative to the average signal response from the non-deposit influenced regions is used to achieve a fourth order polynomial least squares fit 30 through curve fitting techniques. This polynomial is used to determine the thickness of the deposit along specific, user selectable, lengths of tubing between adjacent support structures within a steam generator. The method is structured to utilize calibration standard data acquired during the examination of steam generator tubes. This collection of tube examinations is known as a calibration group. By utilizing the deposit calibration data for the calibration group, the polynomial yields more reliable results wherein variations in the eddy current probe performance are accounted for within the least squares fit. Moreover, the error in the measured thickness, attributed to probe performance, can be quantified for the calibration group. Conventional practice for measurements use a voltage normalized response from a flaw or set of flaws within an ASME calibration standard to establish consistency of probe performance prior to the tube examinations. In these conventional practices, no rigorous process for performing a specific calibration for deposit thickness, as described herein, currently exists, therefore conventional practices are more prone to error.

The next step in the methodology is the establishment of the non-deposit influenced null reference amplitude value for each tube examination data set 40. For probe hardware in conventional applications, balancing is performed independent of the calibrations and consequently the use of such absolute signal amplitude values yields inconsistent and inaccurate results. The establishment of the reference amplitude for each tube 40 with known calibrated values as provided in the present invention represents a significant advantage over conventional applications for measuring the thickness of the deposit by use of low-frequency eddy current. As previously described, the deposit thickness is evaluated using specific, user selectable, lengths of tubing between adjacent support structures within a steam generator. These user selectable lengths are referred to as "bins" within the deposit mapping process and may have a length between ½ inch and 5 inches. Given the user selectable "bin" length, the quantity of eddy current signal amplitudes that constitute a "bin" is determined. For each pair of adjacent support structures, for example tube support one (TSP 1) and tube support two (TSP 2), the quantity of "bins" that can be fitted between the pair is determined 50. For each analysis section, the average signal amplitude is tabulated and for each support pair, the minimum "bin" amplitude is determined. The population of minimum "bin" amplitudes is passed to a culling algorithm to determine the best amplitude value to use as the non-deposit influenced null reference amplitude value for the two. The population of minimum "bin" amplitudes for a circulating steam generator with eight support plates is 16, and the population of a once through steam generator with 15 support plates is 16 in the exemplary embodiment. The culling algorithm requires no less than three "bin" amplitudes to establish the reference amplitude value. If the culling algorithm cannot produce a reference amplitude value, the tube is eliminated from the deposit mapping process.

The criteria of a minimum of three "bin" amplitudes, in the exemplary embodiment, was selected after performing a minimal amount of comparisons of tube results from tubes that had multiple examinations within an outage and tubes with examinations within sequential outages. The consistent measurement of the deposit loading for this minimal population of tubes supported the criteria. An increase in the required minimum quantity of "bin" amplitudes would improve the consistency of the results for a larger population of tube comparisons but would also eliminate a larger number of tubes from the overall deposit mapping process for generators with greater deposit loadings. The culling process is presented using the BASIC programming language:

```
Dim pair_min_value(1 To 32) As Long
'number of pairs used for the base value determination will be initially set
to the number of support pairs (number_of_pairs).
Dim num_mins As Integer
Dim base_value As Long        'the final result (reference value)
Dim spread As Long            'difference between the max and min
Dim max_min As Long              'used to compute the median
Dim min_min As Long           'used to compute the median
Dim median As Long            'used to compute the median
Dim max_min_index As Integer      'used to remember the max value
Dim min_min_index As Integer      'used to remember the min value
Dim i_long As Integer         'general purpose index variable
Dim i_long As Integer         'general purpose Index variable
spread = 31       'force the first pass through the algorithm
num_mins = number_of_pairs
```

The amplitude spread control of 30 equates to a final result of +/−0.001 Inch of deposit thickness from the population average. This value could be adjusted upward to allow for more inclusion or adjusted downward to produce greater exclusion of the members from the final result.

```
While spread > 30 And num_mins > 2
    base_value = pair_min value(1)
    max_min = base_value
    max_min index = 1
    min_min = base_value
    min_min_index = 1
```

The next section of code, the "for/next" loop, is used to identify the maximum and minimum values within the current population of pair minimum values and to sum the values for the calculation of the average.

```
For i_long = 2 To num_mins
    If pair_min_value(i_long) > max_min Then
        max_min = pair_min value(i_long)
```

-continued

```
    max_min_index = i_long
End If
If pair_min_value(i_long) < min_min Then
    min_min = pair_min_value(i_long)
    min_min_index = i_long
End if
    base_value = base_value + pair_min value(i_long)
Next i_long
```

The next three statements calculate the average value, median value, and the spread for the current population of pair minimum values.

```
base_value = CLng(base_value / num_mins)    'the average
median = CLng((max_min + min_min) / 2)       'the median
spread = max_min – min_min                    'the spread
```

The next section of code determines whether the population needs to be culled and if so, which member or members of the population need to be eliminated.

```
If spread > 30 Then        'must reduce the population
If base_value > median Then . 'toss out the low value
i_long = min_min_index
For i_long = i_long To (num_mins –1)
pair_min_value(i_long)=pair_min_value(i_long + 1)
Next i_long
num_mins = num_mins –1
End if
If base_value < median Then      'toss out the high value
i_long = max_min_index
For i_long = i_long To (num_mins –1)
pair_min_value(i_long) = pair_min_value(i_long + 1)
Next i_long
num_mins = num_mins – 1
End If
If base_value = median Then      'toss out both values
i_long = min_min_index
For i_long = i_long To (num_mins – 1)
pair_min_value(i_long)=pair_min_value(i_long + 1)
Next i_long
num_mins = num_mins –1
i_long = max_min_index
If i_long > min_min_index Then i_long = i_long – 1
For i_long = i_long To (num_mins – 1)
pair_min_value(i_long) = pair_min_value(i_long + 1)
Next i_long
num_mins = num_mins –1
End if
End If
Wend       'continue to loop until criteria is achieved
```

Chemical analysis of the target tube scale is used to create a deposit simulation material composed of the eddy current reactive components of the actual deposit. A process is used to apply various thickness bands of this deposit simulation material to a section of tubing. The thickness ranges are based on the expected deposit thickness within the steam generator. A bobbin coil eddy current examination of the deposit standard is used to confirm that the eddy current response phase angle is similar to that observed in the available steam generator data. Where there is no chemical analysis or no significant eddy current deposit response from the actual steam generator under investigation, this check would have been based on comparison with plant data that is similar in nature. When the deposit standard eddy current data has been acquired, it is used to develop a polynomial response function that can be used to convert the absolute signal response into a deposit thickness value 50.

Since absolute data is used for measuring the deposit, care must be taken to define the null point or clean offset value of the data. A number of factors including temperature, eddy current instrument offset, probe construction, tube material and wall thickness as well as deposit or scale of redundancies (among others) all interact to determine the absolute eddy current signal response within the tube. Since the majority of these parameters (with exception of the deposit were scale component) will remain approximately constant during a given tube examination, it is possible to identify the baseline signal offset within most tubes 60. Once the baseline offset value(s) have been identified 60, the baseline offset values is then subtracted from the absolute signal response to isolate and extract the component of the signal that is due to the presence of deposits 70. The use of phase discrimination provides an additional tool to eliminate responses that are not associated with the correct phase angle for the deposit signal.

The eddy current data within the tube is rotated so that the deposit response is in the vertical component. After the offset for a tube has been determined 60, it is subtracted from the signal response 70. The remaining vertical component signal is representative of the deposit response. This remaining vertical component is then applied to the calibration standard polynomial function to derive the deposit thickness estimate 80. The thickness achieved through the polynomial is technically more representative of the total deposit accumulation at a given axial location since these actual thickness could vary around the tube circumference. The bobbin probe response integrates all material within its field of view at a given position within the tube.

In summary, a process that has a specific design of a deposit calibration standard, and the use of this calibration standard, and the use of this calibration standard to establish the least squares fitted polynomial to convert signal amplitude into deposit thickness, and the use of a culling algorithm to determine the non-deposit influenced reference signal amplitude for each tube is a significant improvement over existing methods for determining the thickness of the deposit adhered to the outer diameter surface of steam generator tubing.

This technique has been used to map the deposit distribution within several steam generators. It is possible to compare the deposit mapping technique measurements, as described above, to independent results of Corrosion Product Transport (CPT) measurements. As corrosion product transport measurements are expressed as ionic concentrations of corrosion products and the deposit mapping results are based on the actual expected oxide compound, corrosion product transfer measurements are required to be multiplied by a factor of 1.38 to obtain a comparable value in the exemplary embodiment. As will be understood, other factors may be used when comparing corrosion product transport measurements to steam generator mapping analysis based upon factors, such as chemistry of the plant.

The application of the deposit mapping technique to multiple cycle data provides some information on the repeatability of the technique. This section will present a sample of this information to illustrate the performance of the deposit mapping process, the comparison of the corrosion product transport results and the repeatability of the measurements.

The deposit mapping measurements consist of a series of files that provide the tube row, column, x-coordinate, y-coordinate, z coordinate and the deposit thickness measurement. The below excerpt from a typical deposit text file shows the information available. In this case, the samples were provided every 5 inches actually along the tube. The file coordinates are provided in meters.

30 48-0.9992-0.0163 0.16183
30 48-0.9992-0.0163 0.28882
30 48-0.9992-0.0163 0.41582
30 48-0.9992-0.0163 0.54282
30 48-0.9992-0.0163 0.77096
30 48-0.9992-0.0163 0.89797
30 48-0.9992-0.0163 1.02495
30 48-0.9992-0.0163 1.15195
30 48-0.9992-0.0163 1.27896
30 48-0.9992-0.0163 1.42905
30 48-0.9992-0.0163 1.55604
30 48-0.9992-0.0163 1.68304
30 48-0.9992-0.0163 1.81004
30 48-0.9992-0.0163 1.93704
30 48-0.9992-0.0163 2.06403
30 48-0.9992-0.0163 2.19102
30 48-0.9992-0.0163 2.31802
30 48-0.9992-0.0163 2.44502
30 48-0.9992-0.0163 2.57202
30 48-0.9992-0.0163 2.72211
30 48-0.9992-0.0163 2.84912
30 48-0.9992-0.0163 2.97611
30 48-0.9992-0.0163 3.10311
30 48-0.9992-0.0163 3.23011

Figure 1:
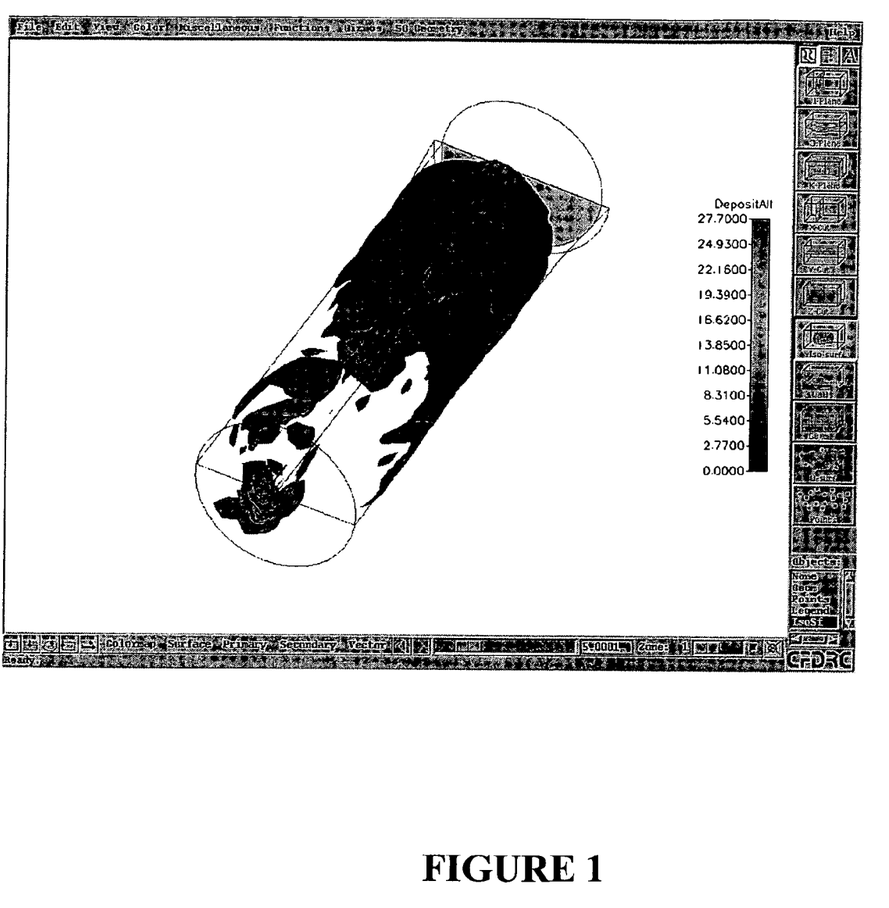
FIG. 1 is a perspective view of a deposit mapping output in conformance with the present invention.
Figure 2:
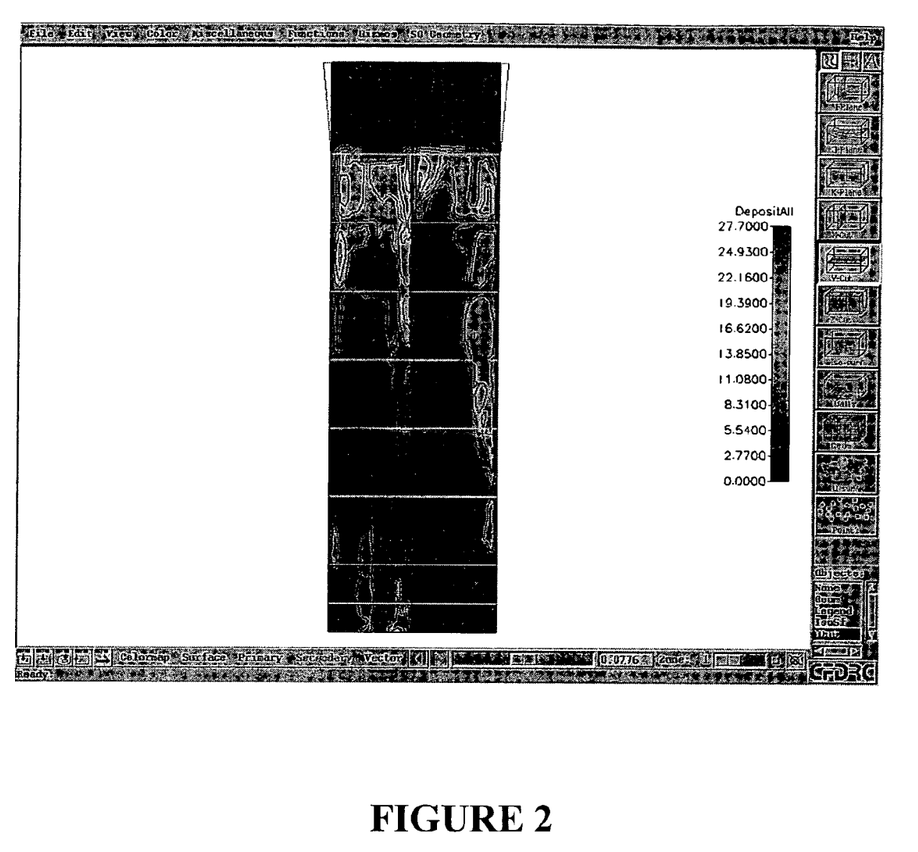
FIG. 2 is a second perspective view of a deposit mapping output.

Referring to FIG. 1, an exemplary deposit mapping output file graphical representation of a deposited tube is provided. Referring to FIG. 2, a second exemplary deposit visualization is provided.

In addition to graphic visualization of the deposit, is also possible to evaluate the overall deposit loading within various locations of the steam generator. The following table 1 provides an example of this type of data. The table lists the results of two separate deposit mapping analysis. In this case, the deposit information has been converted to pounds of deposit.

TABLE 1

|  | 1995 | | 2000 | |
| --- | --- | --- | --- | --- |
| Span | Cold Leg (lbm) | Hot Leg (lbm) | Cold Leg (lbm) | Hot Leg (lbm) |
| 1 (TTS to TSP 1) | 8 | 154 | 7 | 189 |
| 2 (TSP 1 to TSP 2) | 11 | 105 | 10 | 146 |
| 3 (TSP 2 to TSP 3) | 9 | 23 | 15 | 30 |
| 4 (TSP 3 to TSP 4) | 11 | 19 | 35 | 36 |
| 5 ((TSP 4 to TSP 5) | 13 | 27 | 66 | 89 |
| 6 (TSP 5 to TSP 6) | 13 | 37 | 95 | 158 |
| 7 (TSP 6 to TSP 7) | 21 | 42 | 148 | 188 |
| Total | 86 | 407 | 376 | 836 |
| Grand Total | 493 | | 1212 | |

Figure 3:
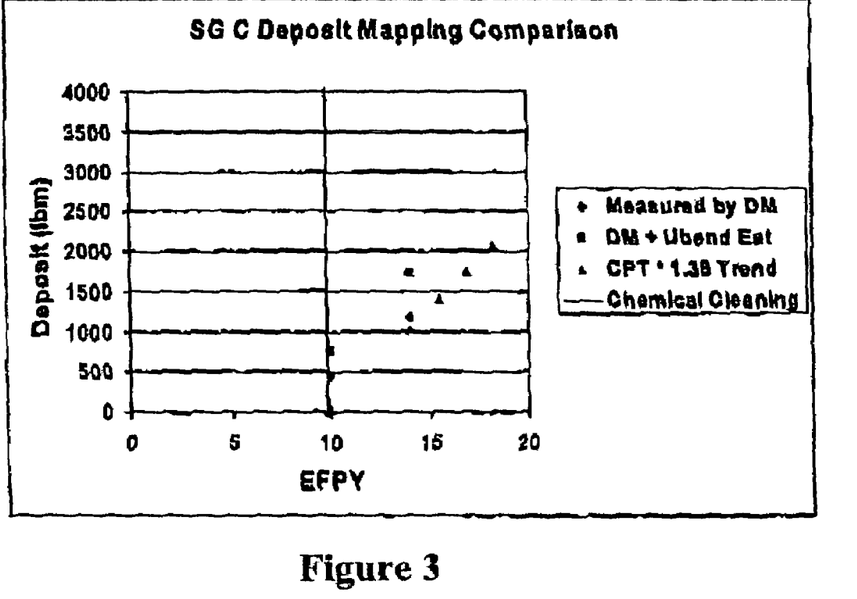
FIG. 3 is a graph comparing deposit mapping to corrosion product transport mechanisms.

FIG. 3 provides a comparison of the deposit mapping estimate of loading with that approximated by CPT. The deposit mapping measurements indicated by the highlighted areas show that the deposit loading, increased by about 956 pounds between 10 and 14 effective full power years of operation. The CPT data, corrected for oxides, provides a standard for comparison and shows an increase of 996 pounds over the same time period verifying the accuracy of the deposit mapping estimate.

An additional advantage of the present invention is measurement repeatability. When measurements are taken over a time interval during which some of the measures are expected change, the repeatability is more difficult to quantify. Eddy current has been used for many years to evaluate the change in indications over a certain time period. The evaluation of such change involves an initial measurement of the start of an interval and a final measurement at the end of the interval.

Statistically, the uncertainty of the measurement technique is included in each initial and final measurement. Thus, the measurement uncertainty for the technique will cause some of the measured indications to have an apparent negative growth even though negative growth is physically impossible. Thus, this apparent negative growth is an indicator of the uncertainty or error of the measurement technique. In the absence of the known values, this apparent negative growth factor may be used to evaluate the reliability of the measurement technique.

Figure 4:
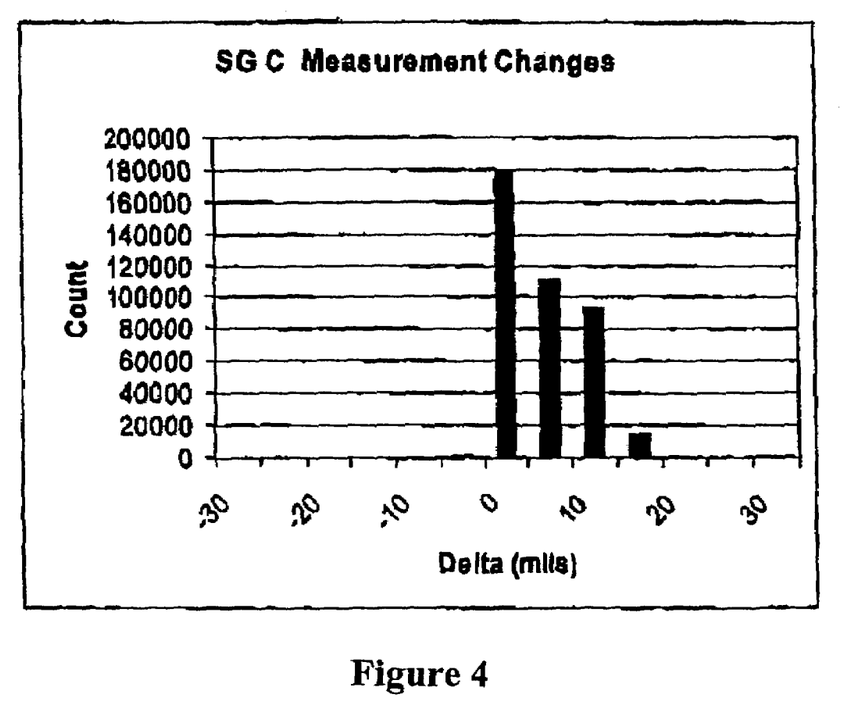
FIG. 4 is a histogram showing deposit mapping repeatability.

FIG. 4 illustrates the measured changes for a large series of initial and final measurement pairs. In the exemplary embodiment provided, as the measurements were taken during a time span when the deposit was expected to increase over time, the expected true delta's (differentials) would have been either zero or positive depending on the location within the steam generator. The extremely small percentage and small value of any negative measurement changes in FIG. 4 is indicative of excellent system reliability and repeatability. If the system uncertainty were higher, the number and magnitude of negative deltas would have been greater.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method to determine deposits in a steam generator, comprising:
    creating a calibration standard having at least two rings of deposit material;
    subjecting the calibration standard to an eddy current signal, wherein an amplitude of the signal reflected from the calibration standard is used to obtain a polynomial equation fit of the reflected eddy current signals to actual thickness of the rings;
    obtaining a steam generator with tubes;
    initiating an eddy current signal into the tubes of the steam generator;
    detecting and recording reflections of the eddy current signal initiated into the tubes of the steam generator; and
    determining a thickness of the deposits in the steam generator from the recorded reflections of the eddy current signal using the polynomial equation fit.

2. The method according to claim 1, wherein the eddy current signal is created by a bobbin coil probe.

3. The method according to claim 1, wherein the polynomial equation fit is a fourth order equation.

4. The method according to claim 1, wherein multiple signals are input into the calibration standard and reflected signals are detected and processed to obtain the polynomial equation fit.

5. The method according to claim 1, wherein the multiple reflected signals are passed through a culling algorithm.

6. A method to determine deposits in a steam generator, comprising:
    creating a calibration standard having at least two rings of deposit material;
    subjecting the calibration standard to an eddy current signal, wherein an amplitude of the signal reflected from the calibration standard is used to obtain a polynomial equation fit of the reflected eddy current signals to actual thickness of the rings;

obtaining a baseline signal offset from the calibration standard;

obtaining a steam generator with tubes;

initiating an eddy current signal into the tubes of the steam generator;

detecting and recording reflections of the eddy current signal initiated into the tubes of the steam generator;

subtracting the baseline signal offset from the reflected eddy current signals to obtain a corrected reflected eddy current signal; and determining a thickness of the deposits in the steam generator from the corrected reflected eddy current signal through the polynomial equation fit.

* * * * *